United States Patent [19]

Christie et al.

[11] Patent Number: 5,759,861
[45] Date of Patent: Jun. 2, 1998

[54] DETECTION OF SULPHUR CONTAINING COMPOUNDS

[75] Inventors: Tony John Christie; Alan Townshend, both of Hull; Andrew Nicholas Trethewey, Salisbury, all of Great Britain

[73] Assignee: Secretary of State for Defence in her Britannic Majesty's Government of the U.K. of Gt. Britain & Northern Ireland of Defence Evaluation & Research Agency, United Kingdom

[21] Appl. No.: 776,641
[22] PCT Filed: Sep. 27, 1995
[86] PCT No.: PCT/GB95/02288
 § 371 Date: Feb. 5, 1997
 § 102(e) Date: Feb. 5, 1997
[87] PCT Pub. No.: WO96/10169
 PCT Pub. Date: Apr. 4, 1996

[30] Foreign Application Priority Data

Sep. 28, 1994 [GB] United Kingdom .................. 9419659

[51] Int. Cl.$^6$ ..................................... G01N 30/74
[52] U.S. Cl. ........................ 436/119; 436/172; 436/120
[58] Field of Search ............................ 436/104, 119, 436/164, 172; 422/82.05, 82.02, 82.08

[56] References Cited

FOREIGN PATENT DOCUMENTS

WO 85/02679  6/1985  European Pat. Off. .

OTHER PUBLICATIONS

Analytical Proceedings, Jan. 1989, vol. 26; Lancaster et al; 'Flow Injection Determination of Organosulphur Compounds with Chemiluminescence Detection'.

Primary Examiner—Lyle A. Alexander
Attorney, Agent, or Firm—Nixon & Vanderhye

[57] ABSTRACT

A method is taught for the detection of organosulfur compounds relating to bis-(2-chloroethyl)- sulphide. The detection can be achieved at trace levels or above and is particularly important in the field of environmental, biological and medical analysis.

27 Claims, 3 Drawing Sheets

DETECTION OF SULPHUR CONTAINING COMPOUNDS

The present invention relates to a method for the detection of specific organosulphur compounds which is capable of distinguishing selected compounds from more common sulphur containing compounds eg. naturally occurring compounds such as sulphur containing amino acids. The determination of such compounds, preferably at trace levels or above, is particularly important in the fields of environmental, biological and medical analysis.

A number of liquid phase chemiluminescence procedures have been developed for the determination of inorganic and organic species mostly utilising the luminol and peroxyoxalate reactions (Robards K. and Worsfold P. J., Anal. Chim. Acta, 1992 266 147), however, other chemiluminescence reactions have been discovered, eg. certain organosulphur species have been found to give rise to chemiluminescence (Lancaster J. S. and Worsfold P. J. Anal. Proc., 1989 26 19). The present invention provides methods which are capable of distinguishing a specific group of organosulphur compounds over other organosulphur compounds such as cysteine and cystine.

The determination of sulphur mustard, bis-(2-chloroethyl)-sulphide, a toxic agent capable of being used in chemical warfare, is of particular importance, both in warfare scenarios and in order to ensure that international laws regulating the use of such agents are not being violated. Thiodiglycol is one of the principal precursors of sulphur mustard manufacture (Lundin S. J. "Verification of Dual-Use Chemicals Under the Chemical Weapons Convention: The Case of Thiodiglycol" 1991 SIPRI) and has been shown to be a major environmental breakdown product of sulphur mustard via hydrolysis (Black R. M., Clarke R. J., Read R. W. and Reid M. T. J., J. Chromatogr., 1994 662 301), as well as being present in biological samples of persons poisoned by sulphur mustard (Wils E. R. J., Hulst A. G., de Jong A. L., Verweij A. and Boter H. L., J. Anal. Tox., 1985 9 254). Thus, the ability to detect this and other hydrolysis products of sulphur mustard eg. 2-chloro-2-hydroxydiethyl sulphide, is also valuable as an indication of the clandestine use of the active agent.

The need for the reliable determination of these compounds has led to the development of a number of sophisticated instrumental methods, mostly involving the use of gas chromatography-mass spectrometry (GC-MS) or GC-MS-MS. These use various modes of ionisation for identification and quantification and particularly use the detector in the selected ion monitoring mode for screening purposes, however, derivatisation procedures are required for the analysis of thiodiglycol. Sulphur mustard and its degradation products possess poor absorptive properties and do not fluoresce in the ultraviolet or visible regions of the electromagnetic spectrum, therefore common liquid phase methods of detection have limited applications, with the need for derivatisation again often necessary. No sensitive liquid phase systems have yet been made available which provide the necessary selectivity required for the direct determination of sulphur containing compounds such as sulphur mustard and thiodiglycol.

The high toxicity of such compounds means that their detection at low levels is of particular value. The method of the invention is capable of detecting thiodiglycol present in a sample at a concentration of 0.2 μg ml$^{-1}$(2×10⁶M), however, the method will also be of value for the detection of organosulphur compounds present in a sample at a concentration of 1 μg ml$^{-}$. The method is therefore much more sensitive than the earlier method studying chemiluminescence, described by Lancaster and Worsfold, which quotes a theoretical detection limit for 2-ethylthiophenol of $4\times10^{-4}$M and which gives examples showing light emission below $2\times10^{-2}$M and very low emission below $5\times10^{-3}$M.

According to this invention a method for determining the presence and/or amount of at least one compound associated with bis-(2-chloroethyl)-sulphide in a sample comprises the steps of i) adding an oxidising agent to the sample ii) measuring the chemiluminescence produced and relating the chemiluminescence produced to the presence and/or amount of compounds associated with bis (2-chloroethyl)-sulphide in the sample.

The compounds detected may be associated with the formation of bis-(2-chloroethyl)-sulphide (eg reactants, by-products), or may be decomposition products and include 1,2-bis (2-chloroethylthio) ethane, bis-(chloroethylthioethyl) ether and thiodiglycol.

A preferred embodiment includes the step of hydrolysing the sample prior to addition of the oxidising agent and allows detection of, for example, compounds which may be hydrolysed to thiodiglycol eg. 2-chloro-2-hydroxydiethylsulphide and bis-(2-chloroethyl)-sulphide.

A further preferred embodiment includes the steps of adding a reducing agent to the sample after measuring the chemiluminesence, said reducing agent being capable of reducing thiodiglycolsulphoxide to thiodiglycol, measuring the chemiluminesence of the sample again and relating the difference in chemiluminesence of the sample before and after addition of said reducing agent to the amount of thiodiglycolsulphoxide present in the sample prior to treatment.

More preferably the reducing agent is titanium tetrachloride.

Measurements made after hydrolysis of the sample will reflect the total amount of thiodiglycol and its hydrolysable precursors present. The amount of precursors can be determined from the difference between the signals measured before and after hydrolysis. However for the purposes of screening for mustard gas and its breakdown products a positive result is sufficient and quantitative measurements are not necessary.

A sensitiser, ie. a fluorescent species capable of increasing the intensity of the chemiluminescent signal, may be added to the sample before chemiluminescence is measured. The addition of such highly fluorescent compounds to a chemiluminescent system is known to enhance relatively weak signals via energy transfer to the fluorescent molecule according to the following set of equations:

$$A+B \rightarrow P^*$$

$$P^*+F \rightarrow F^*+P$$

$$F^* \rightarrow F+h\nu$$

wherein F represents the fluorescent molecule

A and B are the initial reactants

P* is an electronically excited state product

Suitable sensitisers include xanthenes and their derivatives and salts, (eg Rhodamine B, Fluorescein, Rose Bengal and Calcein). Azines, eg. phenosafranine and thiazine derivatives (see Dictionary of Analytical Reagents, Townsend A, Burns DT, Lobinski R, Guilbault GG Newman Ej, Marnzenko Z, Onishi H; p774, (1993), Chapman and Hall, London, New York) are also suitable sensitisers including phenazathiozoniums and their derivatives. Methylene blue is particularly useful. A preferred embodiment of the invention utilises Rhodamine B to increase the chemiluminescent signal by more than 100 times.

Suitable oxidising agents for use in the method of the invention are those capable of oxidising divalent sulphur without interfering with the chemiluminescent emission, examples include hypochlorites, eg. sodium hypochlorite.

The chemiluminescence may be measured using a light detector, eg. a photomultiplier or a solid state photodiode. The chemiluminescence is suitably measured between 550 and 650 nm. One preferred embodiment of the invention provides a method in which the chemiluminescence is measured between 590 and 600 nm.

Preferred methods of the invention are capable of detecting 1 μg ml$^{-1}$ thiodiglycol or precursor in a sample. More preferred embodiments can detect 0.2 μg ml$^{-1}$ or more thiodiglycol or precursor in a sample.

Preferred methods of the invention are those in which the sensitiser and the oxidant are both in solution. The sample and the oxidant may conveniently be introduced into a two stream flow injection system to provide a cheap and easy to use screening system. The oxidant is conveniently introduced into the system in an oxidant stream and the sample in a carrier stream, which in preferred embodiments further comprises a sensitiser. Preferably the carrier stream is non-aqueous, eg alcohols or ketones may be used, particularly aliphatic alcohols and ketones. In preferred embodiments of the invention the oxidant stream comprises lower alkyl alcohols or ketones eg. methanol or acetone.

The optimum pH for the oxidising step will depend on factors such as the medium in which the method is performed. In particular embodiments of the invention pH values between 8 and 12 are preferred, pH values between 8.5 and 11 are more preferred and pH values between 8.5 and 10.5 are the most preferred. When the method is performed using a flow system as described above the oxidant stream will preferably have a pH value between 8 and 12, more preferably between 8.5 and 11, and most preferably between 8.5 and 10.5.

When a flow system is used the reproducibility of results may be poor because of inefficient mixing of the two streams. The addition of a surfactant, preferably a non-ionic surfactant, to the system may at least partially overcome such problems. Polyethylene glycols are suitable surfactants for this purpose, particularly polyoxyethylene ethers, eg. Triton®X-100 and Triton® CF 10. The surfactant is preferably added at a concentration above its critical micelle concentration. If a surfactant or a sensitiser is used it may conveniently be included in the carrier stream.

When a flow system is used the ratio at which the streams are mixed may affect the intensity of chemiluminescent signal obtained. In preferred embodiments of the invention the carrier:oxidant flow ratio is preferably above 1:1, more preferably it is between 1:1 and 2:1, most preferably between 1.3:1 and 2:1. When a flow system is used a pumping device may optionally be included in order to circulate flows through the system to a light detector device.

The present invention further provides apparatus for the determination of the presence and/or amount of at least one compound associated with bis-(2-chloroethyl)-sulphide in a sample comprising a means for adding oxidising agent to the sample, a means of measuring the chemiluminescence produced after addition of said agent and a means for indicating the chemiluminescence measured.

In a preferred embodiment the apparatus includes means for hydrolysing the sample.

The apparatus may conveniently be portable. The means for measuring the chemiluminescence measured will suitably provide a signal the magnitude of which is related to the concentration of compound or compounds of interest in the sample.

The methods and apparatus of the invention will now be illustrated by example only with reference to the following non-limiting Examples and Figures. Further embodiments will occur to those skilled in the art in the light of these.

EXAMPLE 1
DETECTION OF SULPHUR SPECIES

The reagents used in this and subsequent examples were of analytical grade unless stated otherwise. Water used was distilled and deionised. All the solvents were of HPLC grade and were degassed by helium purge before use.

A carrier composition containing $5\times10^{-4}$M Rhodamine B (Fluka, indicator grade, used as obtained) and $2.4\times10^{-4}$M Triton® X 100 (Fluka) in methanol was prepared. An oxidant composition comprising 1.0 M sodium hypochlorite (BDH;GPR; standardised to determine the available hypochlorite by a titrimetric method) in water was prepared at pH 10.0.

$1\times10^{-4}$M methanolic solutions of the following organo-sulphur compounds were prepared: 2,2'-Thiodiglycol (Aldrich; 99+%), diethyl sulphide (Fluka), 3,3'-thiodipropionic acid (Lancaster), diethyl sulphone (Aldrich), divinyl sulphone (Lancaster), DL-cysteine (Sigma), DL-cystine (Sigma), DL-methionine (Sigma) and 1,4-dithiane (Lancaster).

Figure 1:
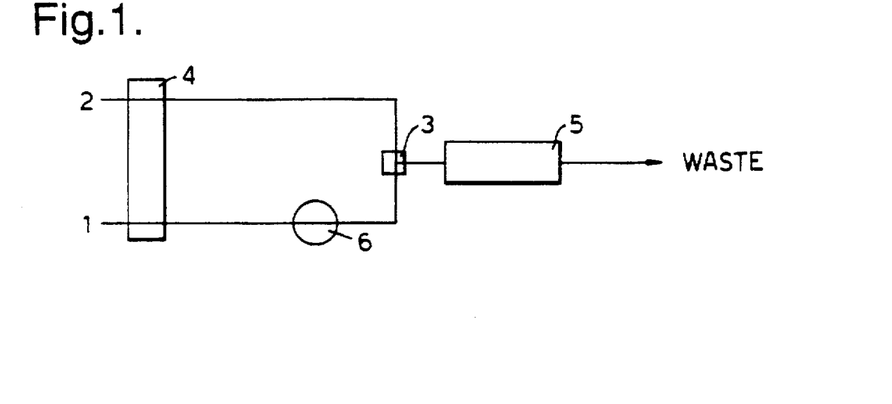
FIG. 1 shows a diagrammatic representation of the apparatus described in Example 1.

A flow system according to FIG. 1 was set up to deliver the carrier stream 1 and the oxidant stream 2 to a polytetrafluoroethylene T-piece 3 using a peristaltic pump (Gilson Miniplus 3) 4 and teflon tubing (0.5 mm id).

The oxidant stream was passed directly to the T-piece at a rate of 0.60 ml min$^{-1}$. The carrier stream was passed to the T-piece at a rate of 0.90 ml min$^{-1}$ 50 μl samples of the organosulphur compounds were injected into the carrier system via an injection valve 6 located 170 mm from the T-piece using a rotary valve (Rheodyne 5020).

The mixed streams were then passed into a coiled glass flow cell (330 gl, 1.5 mm i.d., (not shown)) positioned 20 mm from the T-piece. A photomultiplier tube 5 (Thorn EMI 9924B) within a light tight area (not shown) was used to detect the chemiluminescent emission. The photomultiplier 5 was operated at −900 V, provided by a stable high voltage power supply (Wallis Hivolt, PM2). The response was recorded on a chart recorder (Kipp and Zonen, BD 111) and the results obtained are shown below in Table 1, as chemiluminescent response relative to thiodiglycol, per mole of sulphur within the molecule.

TABLE 1

RELATIVE CHEMILUMINESCENCE RESPONSES OBTAINED FOR VARIOUS SULPHUR SPECIES

| Species | | Relative Peak Height (per mole S) |
|---|---|---|
| Bis(2-hydroxyethyl)-sulphide | TDG | 100.0 |
| Bis(2-chloroethyl)-sulphide | H | 8.5 |
| Ethyl-2-hydroxyethyl sulphide | | 78.2 |
| 1,2-Bis(2-chloroethylthio)ethane | Q | 8.8 |
| Bis(2-chloroethylthioethyl)ether | T | 5.5 |
| 2-Chloroethyl-2-hydroxyethyl sulphide | | 23.6 |
| Mercaptoacetic Acid | | 6.5 |
| 2-Chloroethylethyl sulphide | | 5.4 |
| Divinyl sulphoxide | | Equivalent to blank |
| Divinyl sulphone | | 0.6 |
| 1,4-Thioxane | | 0.6 |
| 1,4-Dithiane | | 2.0 |
| Diethyl sulphide | | 0.5 |
| Diethyl sulphone | | 0.6 |
| 3,3'-Thiodipropionic acid | | 1.0 |
| Cysteine | | 4.0 |
| Cystine | | 0.9 |
| Methionine | | Equivalent to blank |
| Dimethoate | | 5.9 |
| Cyanophos | | 1.5 |
| Dimethyl sulphoxide | | 1.9 |
| Di-n-Propyl disulphide | | 1.2 |
| 2,5-Dihydroxy-1,4-dithiane | | 0.4 |
| 2-Mercaptoethyl ether | | Equivalent to blank |
| 2-Ethylthiophenol | | Equivalent to blank |
| Diphenyl sulphide | | Equivalent to blank |
| 2-Mercaptoethanol | | Equivalent to blank |
| Sulphide anion | | Equivalent to blank |

The results given in Table 1 show a surprisingly high selectivity towards thiodiglycol in the detection method. Ethyl-2-hydroxyethyl sulphide and 2-chloroethyl-2-hydroxyethyl sulphide gave the next highest responses: all other compounds tested had a relative peak height of less than 10 (where 2,2'-thiodiglycol had a relative peak height of 100). DL-Methionine, divinyl sulphoxide, 2-mercaptoethyl ether, 2-ethylthiophenol, 2-mercaptoethanol gave a negative response (equivalent to a blank injection of methanol), as did the sulphide anion, which was tested in order to check that chemiluminescent emission did not occur as a result of low levels of sulphide impurities in the analytical standards.

EXAMPLE 2
DETECTION OF DIFFERENT CONCENTRATIONS OF THIODIGLYCOL.

Figure 2:
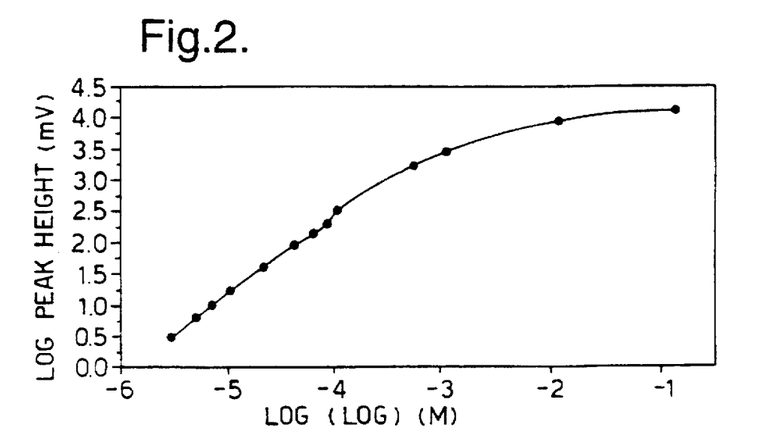
FIG. 2 shows a graph of Log(peak height of chemiluminescent signal) versus Log[thiodiglycol].
Figure 3:
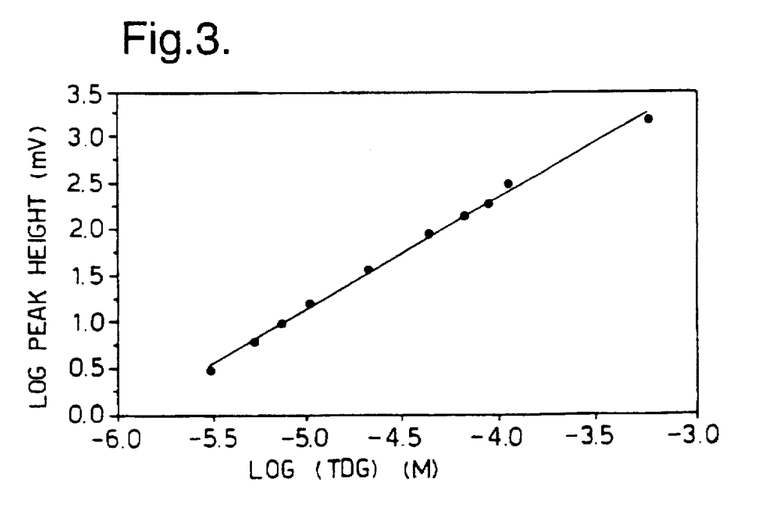
FIG. 3 shows the linear range of a graph of Log(peak height of chemiluminescent signal) versus Log [thiodiglycol].

Samples of thiodiglycol ranging from $3\times10^{-6}$M to $1.1\times10^{-1}$M were prepared and their chemiluminescence determined according to the method described in Example 1. A log-log plot of mean peak height of the chemiluminescent emission against concentration of thiodiglycol (mol F1) was plotted and is given in FIG. 2. The plot was found to be linear between $3\times10^{6}$M and $5\times10^{-4}$M, as shown in FIG. 3; from this part of the plot the following characteristics of the method were determined.

log (peak height) 1.2 log [TDG] +7.4
r=0.9982 (n=10)

Detection limit=$2\times10^{-6}$M (in 50 µl≡100pmol) (3× standard deviation of lowest response)
% rsd=1.6% (n=10; [TDG] =$4\times10^{-5}$M)

EXAMPLE 3
EFFECT OF SOLVENT ON THE CHEMILUMINESCENCE OF THIODIGLYCOL

A flow system as described in Example 1 was prepared, omitting the Rhodamine B and Triton® X-100. Different solvents were used in the carrier stream in order to study their effect on the chemiluminescent signals from the oxidation of $1\times10^{-2}$M solutions of thiodiglycol; these were measured and the results obtained are given below in Table 2. The solvents used required different concentrations of hypochlorite to obtain optimum chemiluminescent emission, probably due to the presence of other oxidisable species in the flow system, eg. the carrier solvent.

TABLE 2

THE EFFECT OF SOLVENT ON THE CHEMILUMINESCENCE AND THE CONCENTRATION OF HYPOCHLORITE REQUIRED FOR THE BEST CHEMILUMINESCENT RESPONSE

| Solvent | [hypochlorite] | Relative peak | Dielectric |
|---|---|---|---|
| methanol | 1.0 | 42.6 | 32.6 |
| ethanol | 1.0 | 36.0 | 24.3 |
| acetonitrile | 0.5 | 1.46 | 37.5 |
| water, $CO_3^{2-}$buffer | $1 \times 10^{-2}$ | 5.43 | 78.5 |

EXAMPLE 4
ADDITION OF SURFACTANTS IN THE METHOD OF DETERMINING THIODIGLYCOL

A flow system as described in Example 1 was prepared, omitting the Rhodamine B from the carrier stream. Surfactants other than Triton® X100 were added to the carrier stream in order to ascertain whether they could be used to aid the mixing process further and allow the precision of the method to be improved. Aqueous solutions of an anionic surfactant sodium dodecyl sulphate (SDS), a cationic surfactant Cetyltrimethyl ammonium bromide (CTAB) and the non-ionic surfactant Triton® X-100 (TX) were prepared above their critical micelle concentrations (cmcs). These were added to the methanolic carrier stream rather than the oxidant stream to eliminate the possibility of prior oxidation of the surfactant by the hypochlorite solution. Their effect on the chemiluminescent signals from the oxidation of $1\times10^{-2}$M solutions of thiodiglycol, were measured and the results obtained are shown below in Table 3.

TABLE 3

THE EFFECT OF THE ADDITION OF DIFFERENT SURFACTANTS TO THE CARRIER SYSTEM ON THE CHEMILUMINESCENT RESPONSE

| Carrier stream | Relative | Surfactant | cmc |
|---|---|---|---|
| methanol | 1.00 | — | — |
| methanol + SDS | ppt | $1.14 \times 10^{-2}$ | $8.1 \times 10^{-3}$ |
| methanol + CTAB | 0 | $1.12 \times 10^{-3}$ | $9.2 \times 10^{-4}$ |
| methanol + TX | −0.18 | $3.8 \times 10^{-4}$ | $2.4 \times 10^{-4}$ |

These results indicate that both cetyltrimethylammonium bromide and Triton® X-100 quench the chemiluminescent emission. The addition of sodium dodecyl sulphate to the system resulted in the formation of a precipitate at the T-piece and it was necessary to dismantle the detector to remove the blockage.

EXAMPLE 5
ADDITION OF VARIOUS SENSITISERS TO THE METHOD OF DETERMINING THIODIGLYCOL

A flow system as described in Example 1 was prepared using a carrier stream without surfactant. Aqueous solutions of various fluorophores were prepared ($1\times10^{-4}$M in pH 11.0 carbonate buffer) and added to the carrier system such that the carrier stream contained methanol:water (50:50). Their effect on the chemiluminescent signals from the oxidation of $1\times10^{-2}$M solutions of thiodiglycol was measured and the results obtained are given below in Table 4.

TABLE 4
THE EFFECT OF SENSITISERS ON THE CHEMILUMINESCENT RESPONSE OF THIODIGLYCOL

| Solution | Relative Peak Height | S/N Ratio |
| --- | --- | --- |
| Blank | 1.0 | 45 |
| Calcein | 104.6 | 10 |
| Rose Bengal | 49 | 18 |
| Riboflavin | 0.9 | 32 |
| Fluorescein | 78.0 | 35 |
| Rhodamine B | 132.2 | 120 |
| Methylene Blue | 99.6 | 62 |

These results show that all the sensitisers except riboflavin gave rise to an enhanced chemiluminescent signal, however only Rhodamine B and Methylene blue increased the signal to noise ratio.

EXAMPLE 6
STUDY OF THE EFFECT OF RHODAMINE B CONCENTRATION ON THE CHEMILUMINESCENT EMISSION

Figure 4:
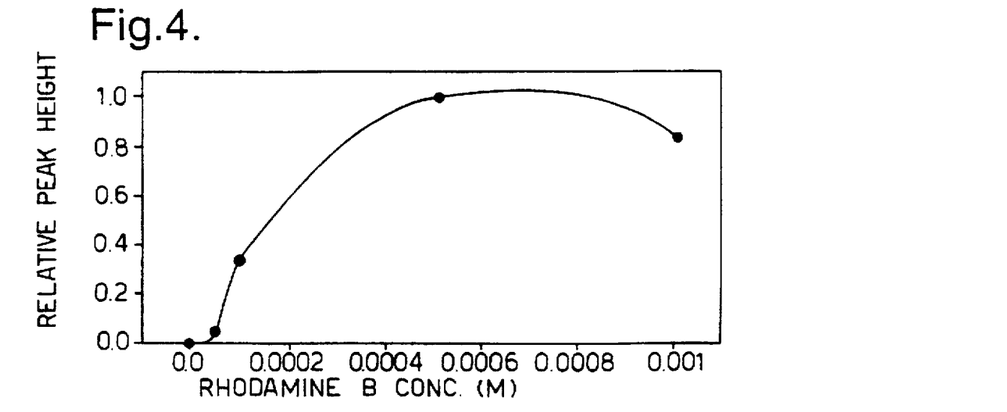
FIG. 4 shows the effect of Rhodamine B concentration on chemiluminescence.

The method described in Example 5 was repeated using only Rhodamine B as the sensitiser (in methanol) but varying its concentration in order to determine the optimum amount to be added. The results obtained are shown in FIG. 4; from these the optimum concentration of Rhodamine B, i.e. that giving the greatest peak height was found to be $5\times10^{-4}$M.

EXAMPLE 7
DETECTION OF THIODIGLYCOL USING A SENSITISER IN THE PRESENCE OF A SURFACTANT

Figure 5:
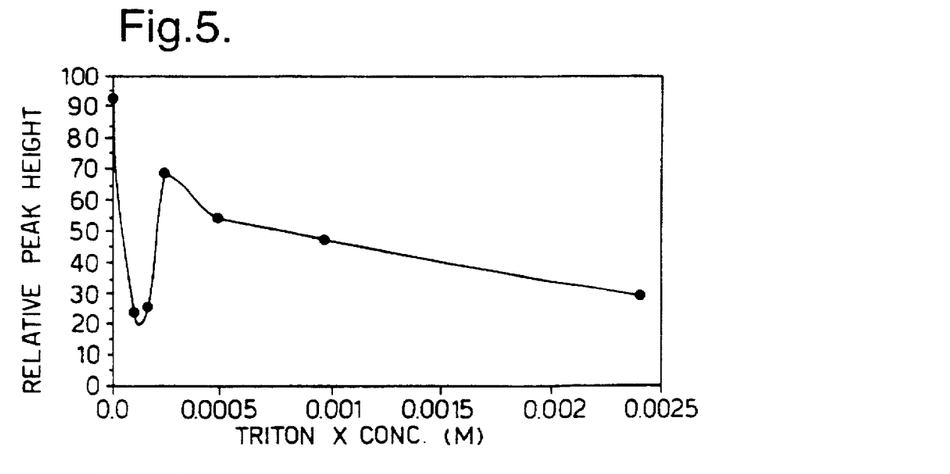
FIG. 5 shows the effect of Triton® X-100 concentration on chemiluminescent signal.

A flow system as described in Example 1 was prepared having Rhodamine B ($5\times10^{-4}$M) and various concentrations of Triton® X-100 in the carrier stream. The effect of the presence of the surfactant on the chemiluminescent signal from the oxidation of $1\times10^{-5}$M solutions of thiodiglycol was measured and the results obtained are shown in FIG. 5. Although the addition of methanolic Triton® X-100 did not enhance the chemiluminescent signal, when added at and above its cmc it was found to greatly improve the between-injection relative standard deviation (rsd) to approximately 3% (n=15). A drop in signal of approximately 25% was observed at a Triton X-100 concentration of $2.4\times10^{-4}$M, and at a Triton X-100 concentration of $2.4\times10^{-3}$M the drop in signal was approximately 70%.

EXAMPLE 8
STATIC CHEMILUMINESCENCE MEASUREMENTS

Figure 6:
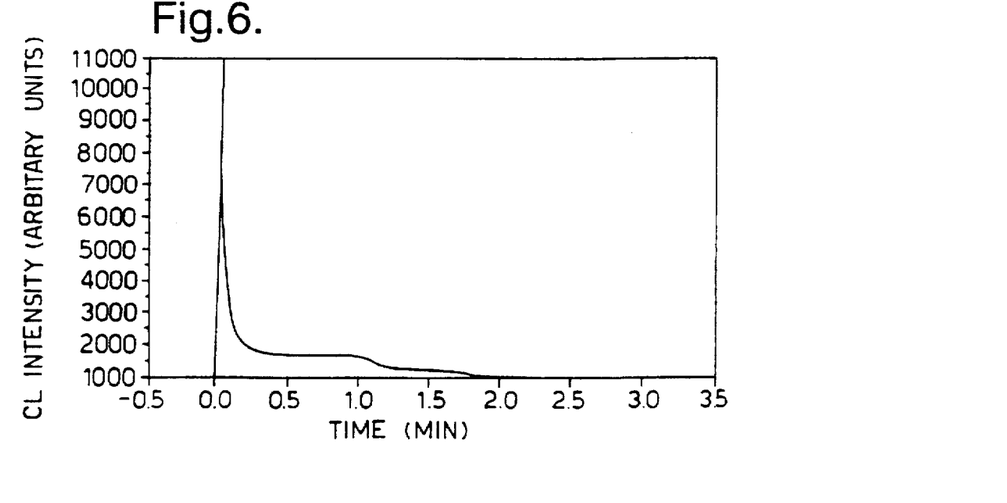
FIG. 6 shows the chemiluminescent signal resulting from the reaction of Rhodamine B with hypochlorite.
Figure 7:
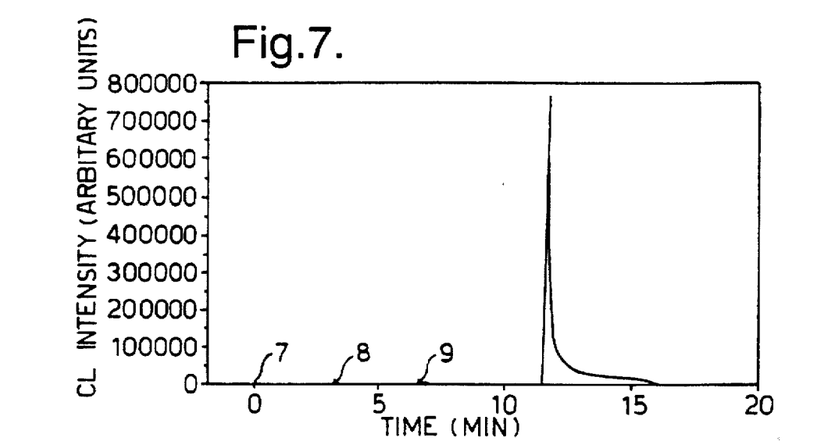
FIG. 7 shows the chemiluminescent decay profiles for three 'blanks' and one with added thiodiglycol ($1\times10^{-2}$M).

Sodium hypochlorite solution was injected into a $5\times10^{-4}$M methanolic Rhodamine B solution using a batch luminometer (Berthold Biolumat LB 9500T) and the chemiluminescence produced recorded. The decay curve obtained is shown in FIG. 6. $1\times10^{-2}$M thiodiglycol solution was added to the methanolic Rhodamine B solution and a substantial increase in chemiluminescence was noted. The comparison of this emission and three blank signals 7, 8 and 9 is shown in FIG. 7.

EXAMPLE 9
STUDY OF THE EFFECT OF pH ON THE DETERMINATION OF THIODIGLYCOL

Figure 8:
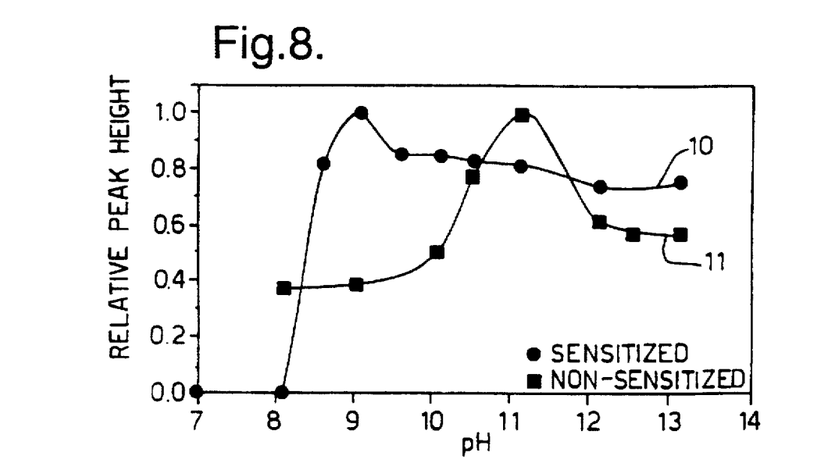
FIG. 8 shows a comparison of the pH dependence of sensitised and non-sensitised systems.

Earlier work performed by Lancaster and Worsfold showed the optimum pH of the hypochlorite solution in the non-sensitised flow system using hydrogen carbonate buffer to be pH 11.0. In shifting from a non-sensitised to a sensitised system a change in pH is often realised (Teckentrup J and Klockow D, Talanta, 1981 28 653). The effect of pH was therefore investigated using hydrochloric acid to adjust the pH because carbonate buffer was found to cause the build up of precipitated matter in the T-piece. A comparison of the two systems (sensitised 10 and non-sensitised 11) is shown in FIG. 8.

The optimum pH value for the sensitised system 10 using Rhodamine B was found to be pH 9.0. However, at pH values of 10–13 the signal remains almost constant and is approximately 75% of the maximum value. pH 10.0 was chosen as a suitable value for the performance of the method of determining thiodiglycol using Rhodamine B as a sensitiser and Triton® X-100 as a surfactant.

EXAMPLE 10
STUDY OF THE EFFECT OF CARRIER:OXIDANT RATIO AND THE FLOW RATE OF THE OXIDANT STREAM ON THE CHEMILUMINESCENT SIGNAL

Figure 9:
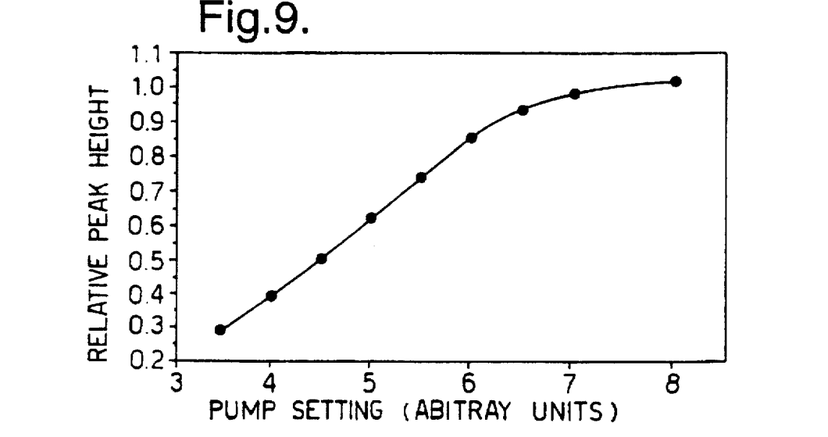
FIG. 9 shows the effect of pump setting on chemiluminescent response.

The ratio of carrier to oxidant flow rate was altered (whilst the total flow rate remained constant) in order to study the effect this had on the chemiluminescent signal obtained and the results obtained are shown below in Table 5. The optimum ratio of 1.4:1 (carrier:oxidant) was then used in order to study the effect of varying the flow rate of this stream on the chemiluminescent signal, the results obtained are shown in FIG. 9.

TABLE 5
THE EFFECT OF CARRIER:OXIDANT FLOW RATIO UPON CHEMILUMINESCENCE RESPONSE

| Carrier:Oxidant Ratio | Relative Peak Height |
| --- | --- |
| 0.7:1 | 0 |
| 1.0:1 | 0.31 |
| 1.4:1 | 1.00 |
| 1.7:1 | 0.89 |

The chemiluminescent signal was found to increase with increasing pump speed, although the between-injection precision was found to worsen, suggesting that the light emission was not occurring reproducibly in a single part of the flow cell. This could be a result of pump pulsing problems encountered at high flow rates. A pump speed of 5.5 (arbitrary units) was considered the most appropriate to investigate the chemiluminescence of thiodiglycol, this pump speed corresponding to a total flow rate of 1.5 ml min$^{-1}$, i.e. oxidant flow of 0.6 ml min$^{-1}$ and carrier flow of 0.9 ml min$^{-1}$. The optimum flow rate will depend on the instrumentation used.

EXAMPLE 11
FURTHER STUDIES OF SENSITISERS

A series of fluorescent compounds was examined for their effect on the flow injection system.

Each compound was dissolved in methanol ($1\times10^{-4}$M, no surfactant present) and the resulting solution was used as a carrier stream. Prior to the use of each compound, a "blank" methanol carrier stream was run through the system so that the background could be recorded upon introduction of each compound. Once the background was noted (over five minutes) injections of TDG ($1\times10^{-4}$M, in methanol) were made and the chemiluminescent emission recorded. From the results, a signal to background ratio for each compound was derived. These data are shown in Table 6 in which "Signal" is the signal arising from an injection of TDG ($1\times10^{-4}$M) with a carrier stream sensitiser concentration of $1\times10^{-4}$M; "Background" is the background signal averaged over five minutes and "S/B" is the signal to background ratio.

TABLE 6

THE EFFECT OF VARIOUS SENSITISERS ON THE CHEMILUMINESCENCE OF TDG

| Sensitiser | Signal (mV) | Background (mV) | S/B |
|---|---|---|---|
| Phenosafranine | 348.5 | 5.0 | 69.7 |
| Rhodamine B | 110.2 | 13.0 | 8.5 |
| Rhodamine 6G | 17.0 | 12.0 | 1.4 |
| Eosin Y | 18.2 | 13.0 | 1.4 |
| Fluoroescin | 269.4 | 38.0 | 7.1 |
| Safranine T | 20.8 | 1.25 | 16.6 |
| Rose Bengal | 129.6 | 60.5 | 2.1 |
| Methylene Blue | 20.5 | 0.5 | 41.0 |
| New Methylene Blue | 64.5 | 9.5 | 6.8 |
| Neutral Red | 0.92 | 0.75 | 1.2 |

The highest signal to background ratio was obtained from the azine dye phenosafranine. The thiazine dye Methylene blue also showed a high signal to background ratio, but at concentrations of TDG lower than $1\times10^{-4}$M the signal is lost in the dark current noise of the photomultiplier tube.

EXAMPLE 12
FURTHER STUDIES OF SURFACTANTS

Eight commercially available non-ionic surfactants were screened in the Flow Injection-Chemiluminesence System by injecting TDG ($1\times10^{-4}$M in methanol) into a Rhodamine B ($5\times10^{-4}$M in methanol) carrier stream containing each surfactant and monitoring the resultant CL emission. The surfactants were of the polyoxyethylene (Tweens) and polyethylene glycol (Tritons and Brij) 35 types.

The concentration of each surfactant was varied so that the optimum concentration for each could be evaluated. This process was conducted because the critical micellar concentration was not known for each individual surfactant. A summary of the results obtained are shown in Table 7 and are expressed as the relative CL intensity (relative to a carrier stream containing rhodamine B ($5\times10^{-4}$M) alone).

TABLE 7

EFFECT OF VARIOUS SURFACTANTS ON CHEMILUMINESCENT INTENSITY

| Surfactant | Rel. CL Intensity | Optimum Conc$^n$. (mg ml$^{-1}$) | rsd % |
|---|---|---|---|
| Triton ® X-45 | 1.0 | 0.17 | 2.19 |
| Triton ® N101 | 1.1 | 0.13 | 1.77 |
| Triton ® CF 10 | 3.2 | 0.65 | 1.35 |
| Triton ® X100 | 1.0 | 0.12 | 1.20 |
| Tween ® 20 | 1.4 | 0.01 | 1.24 |
| Tween ® 60 | 1.1 | 0.01 | 1.88 |
| Tween ® 80 | 1.3 | $5\times10^{-3}$ | 1.11 |
| Brij ® 35 | 1.1 | 0.50 | 0.56 |

The results show that the surfactant Triton® CF 10 gives rise to an approximate three times increase in CL emission intensity. The optimum concentration for this surfactant was found to be 0.65 mg ml$^{-1}$.

Referring to FIG. 10, thiodiglycol 8 has been shown to oxidise to thiodiglycolsulphoxide 9 and thiodiglycolsulphone 10.

In an actual sample, after a period of four years had elapsed since contamination of a soil sample with sulphur mustard, the majority of the reagent had been hydrolysed. It was shown that more than half of the thiodiglycol produced by the hydrolysis had been oxidised to thiodiglycolsulphoxide 9. Only a very small fraction of the thiodiglycolsulphoxide was further oxidised to the thiodiglycolsulphone 10. The chemiluminesence detection method can therefore be further enhanced by introducing the reductive step into the method and converting the thiodiglycolsulphoxide 9 into the thiodiglycol 8. It is relatively easy to reduce thiodiglycolsulphoxide 9 to thiodiglycol 8 by use of titanium tetrachloride. To reduce the thiodiglycolsulphone 10 to thiodiglycol 8 requires much harsher conditions e.g. lithium aluminium hydride but as only a very small amount is produced this is not a problem.

If both the proposed hydrolysis and reductive steps are included in a method then the measurements could provide data on the level of sulphur mustard, thiodiglycol 8 and thiodiglycolsulphoxide 9. The first measurement is carried out without any treatment to obtain data on thiodiglycol. This should be followed by the hydrolysis step and subsequent measurement. This will give levels of sulphur mustard in the sample. Finally the reductive step and the measurement will give data on the thiodiglycolsulphoxide 9 level.

We claim:

1. A method of detecting a compound selected from the group consisting of thiodiglycol, bis-(2-chloroethyl)-sulphide, 1,2-bis-2(-chloroethylthio) ethane, and bis-(2-chloroethylthiethyl) ether that are precursors, by products or degredation products of bis-(2-chloroethyl)-sulphide in a sample, said method comprising the steps of (a) adding an oxidizing agent to the sample, (b) measuring the chemiluminescence produced, and (c) relating the chemiluminescence produced to the presence said compounds in the sample.

2. The method of claim 1 and further comprising the steps of adding a reducing agent to the sample after measuring the chemiluminesence, said reducing agent being capable of reducing thiodiglycolsulphoxide to thiodiglycol, measuring the chemiluminesence of the sample again and relating the difference in chemiluminesence of the sample before and after addition of said reducing agent to the amount of thiodiglycolsulphoxide present in the sample prior to treatment.

3. The method of claim 2 where the reducing agent is titanium tetrachloride.

4. The method of claim 1 where the oxidising agent comprises a hypohalite.

5. The method of claim 4 wherein the oxidising agent is sodium hypochlorite.

6. The method of claim 1 where the chemiluminescence is measured within the range 550 to 650 nm.

7. The method of claim 6 where the chemiluminescence is measured within the range 590 to 600 nm.

8. The method of claim 1, further comprising the step of hydrolysing the sample prior to addition of oxidising agent.

9. The method of claim 8 where at least one compound associated with bis (2-chloroethyl)-sulphide is a precursor to thiodiglycol, capable of being hydrolysed to thiodiglycol.

10. A method as claimed in claim 9 wherein the precursor is 2-chloro-2-hydroxydiethylsulphide or bis-(2-chloroethyl)-sulphide.

11. A method as claimed in claim 1 wherein a sensitiser is added to the sample before the oxidising and measuring steps.

12. The method of claim 11 where the sensitiser is the azine dye phenosafranine.

13. The method of claim 11 where the sensitiser added comprises a xanthene or derivative.

14. The method of claim 11 where the sensitiser added is selected from Rhodamine B, Fluorescein, Rose Bengal, Calcein and their salts.

15. The method of claim 11 where the sensitiser added comprises a phenazathiozonium.

16. The method of claim 15 where the sensitiser added comprises methylene blue.

17. The method of claim 1 where the sample and the oxidant are introduced into a flow injection system: the oxidant being introduced into the system in an oxidant stream and the sample being introduced into the system in a carrier stream.

18. The method of claim 17 where the carrier stream further comprises a sensitiser.

19. A method as claimed in claim 2 where the oxidant stream has a pH value between 8 and 12.

20. A method as claimed in claim 17 where the carrier stream further comprises a surfactant.

21. The method of claim 20 where the surfactant comprises a polyethylene glycol.

22. A method as claimed in claim 17 wherein the carrier:oxidant flow ratio is at, or above, 1:1.

23. The method of claim 22 wherein the carrier:oxidant flow ratio is between 1.3:1 and 2:1.

24. The method claim 17 where the carrier stream is non-aqueous.

25. The method of claim 24 where the carrier stream comprises an alcohol or ketone.

26. The method of claim 25 where the carrier stream comprises methanol or acetone.

27. The method of claim 26 where the oxidant stream has at a pH value between 8.5 and 10.5.

* * * * *

UNITED STATES PATENT AND TRADEMARK OFFICE
CERTIFICATE OF CORRECTION

PATENT NO. : 5,759,861
DATED : June 2, 1998
INVENTOR(S) : Christie et al

It is certified that error appears in the above-identified patent and that said Letters Patent is hereby corrected as shown below:

Column 10, lines 1-27 should read as follows:

--Thiodiglycol has been shown to oxidise to thiodiglycolsulphoxide and thioglycolsulphone.

In an actual sample, after a period of four years had elapsed since contamination of a soil sample with sulphur mustard, the majority of the reagent had been hydrolysed. It was shown that more than half of the thiodiglycol produced by the hydrolysis had been oxidised to thiodiglycolsulphoxide. Only a very small fraction of the thiodiglycolsulphoxide was further oxidised to the thiodiglycolsulphone. The chemiluminescence detection method can therefore be Further enhanced by introducing the reductive step into the method and converting the thiodiglycolsulphoxide into the thiodiglycol. It is relatively easy to reduce thiodiglycolsulpoxide to thiodiglycol by use of titanium tetrachloride. To reduce the thiodiglycolsulphone to thiodiglycol requires much harsher conditions e.g. lithium aluminium hydride but as only a very small amount is produced this is not a problem.

UNITED STATES PATENT AND TRADEMARK OFFICE
CERTIFICATE OF CORRECTION

PATENT NO. : 5,759,861
DATED : June 2, 1998
INVENTOR(S) : Christie et al.

It is certified that error appears in the above-identified patent and that said Letters Patent is hereby corrected as shown below:

If both the proposed hydrolysis and reductive steps are included in a method then the measurements could provide data on the level of sulphur mustard, thiodiglycol and thiodiglycolsulphoxide. The first measurement is carried out without any treatment to obtain data on thiodiglycol. This should be followed by the hydrolysis step and subsequent measurement. This will give levels of sulphur mustard in the sample. Finally the reductive step and the measurement will give data on the thiodiglycolsulphoxide level.--

Signed and Sealed this

Third Day of August, 1999

Attest:

Q. TODD DICKINSON

*Attesting Officer*       *Acting Commissioner of Patents and Trademarks*